United States Patent [19]

Stutz et al.

[11] 4,077,252

[45] Mar. 7, 1978

[54] APPARATUS FOR THE OPTO-ELECTRICAL DETERMINATION OF A MEASURED VALUE

[75] Inventors: Theo Stutz, Bassersdorf; Georg Zemp, Zurich, both of Switzerland

[73] Assignee: Contraves AG, Zurich, Switzerland

[21] Appl. No.: 771,035

[22] Filed: Feb. 22, 1977

[30] Foreign Application Priority Data

Mar. 15, 1976 Switzerland .................. 3226/76

[51] Int. Cl.² ............... G01N 11/14; G01B 11/26
[52] U.S. Cl. .................................. 73/59; 250/230
[58] Field of Search ............ 73/59, 60; 250/230, 250/231 SE

[56] References Cited

U.S. PATENT DOCUMENTS

| | | | |
|---|---|---|---|
| 3,122,914 | 3/1964 | Stabe et al. | 73/59 |
| 3,443,418 | 5/1969 | Tschudin | 73/59 |
| 3,533,275 | 10/1970 | Zemp | 73/59 |
| 3,545,257 | 12/1970 | Zemp et al. | 73/59 |
| 3,836,260 | 9/1974 | Ulyanov et al. | 250/230 X |

FOREIGN PATENT DOCUMENTS

| | | | |
|---|---|---|---|
| 2,271,563 | 12/1975 | France | 73/59 |
| 2,301,083 | 1/1973 | Germany | 73/59 |

*Primary Examiner*—S. Clement Swisher
*Assistant Examiner*—Joseph W. Roskos
*Attorney, Agent, or Firm*—Werner W. Kleeman

[57] ABSTRACT

An apparatus for the opto-electrical determination of a measured value or magnitude at a viscosimeter, especially at a rotational viscosimeter, wherein there is provided a rotatable body immersible in the medium to be measured and connected with the rotor of a motor and a shaft fixably connected for rotation with the stator of the motor and pivotably mounted against the action of the restoring force of a torsion spring. In order to obtain a series of light pulses which are independent of the measured magnitude and to also obtain a further series of light pulses dependent upon the measured magnitude, at least one reflector rotatably driven by a motor about an axis of rotation is arranged in spaced relationship from and essentially axially parallel to the pivotably mounted shaft which itself is equipped with a reflector and a stationary optical block or system is dispositioned in an appropriate geometric arrangement with respect to the rotatably driven reflector. The optical block comprises a light source producing a bundle of light rays directed at the rotatably driven reflector and a light receiver for processing the light pulses.

10 Claims, 8 Drawing Figures

APPARATUS FOR THE OPTO-ELECTRICAL DETERMINATION OF A MEASURED VALUE

BACKGROUND OF THE INVENTION

The present invention relates to a new and improved construction of apparatus for the opto-electrical (also sometimes referred to as the electro-optical) determination of a measured value or magnitude at a viscosimeter, especially a rotational viscosimeter.

There are already known to the art different constructions of and differently operating systems for both measuring and indicating a measurement result during the measurement of the viscosity of a medium by means of a rotational viscosimeter. Two of the state-of-the-art systems will be briefly considered hereinafter. One such system, for instance as taught in Swiss Pat. No. 474,055, imparts a deflection out of a null-position to a rotatably mounted transmission housing owing to the action of the occurring braking moment. The angle of deflection of the housing constitutes a measure for the brake moment and thus for the viscosity of the medium and can be measured, for instance, by means of an electromagnetic system which has become known under the designation "Pick-Off". This measured deflection angle can then be read-off of an indicator device.

According to another prior art system, for instance as disclosed in German Pat. No. 1,648,858, the occurring brake moment is transmitted to a stator shaft which can be rocked against the restoring force of a torsion spring. The stator shaft is rotated out of a rest position together with a measuring indicator attached thereto as a function of the degree of the effective viscosity of the medium which is being measured, so that it is possible to read the viscosity of such medium by means of a suitable scale dial appropriately calibrated in degrees of viscosity and operatively associated with the measuring or measurement indicator.

SUMMARY OF THE INVENTION

It is a primary object of the present invention to provide a new and improved construction of apparatus for the opto-electrical determination of a measured magnitude in an extremely reliable and accurate manner.

Still another and more specific object of the present invention aims at the provision of apparatus for the opto-electrical determination of a measured magnitude at a viscosimeter in an extremely reliable, accurate and relatively simple manner.

Still a further significant object of the present invention aims at the provision of an apparatus for a viscosimeter having a pivotable shaft, by means of which the degree of pivoting or rocking of the shaft can be converted into a time measurement in that the shaft carrying a reflector has correlated thereto at the starting position and the terminal position of its rotation, by utilizing opto-electrical principles, a respective series of light pulses and the phase shift from the one series of light pulses to the other series is measured.

Now in order to implement these and still further objects of the invention, which will become more readily apparent as the description proceeds, the invention contemplates the provision of an apparatus for the opto-electrical determination of a measured magnitude or value at a viscosimeter, especially a rotational viscosimeter, wherein there is provided a rotatable body immersible in the medium to be measured and connected with the rotor of a motor as well as a pivotably mounted shaft rigidly connected for rotation with the stator of the motor and rockable against the restoring force of a torsion spring. According to important aspects of the invention, in order to obtain a series of light pulses which is independent of the measured magnitude as well as to obtain another series of light pulses which is dependent upon the measured magnitude, at least one reflector which is rotatably driven about an axis of rotation by a motor is arranged in spaced relationship from and essentially axially parallel to the pivotably mounted shaft which also is equipped with a reflector. Further, a stationary optical block or system is disposed in appropriate geometrical arrangement with regard to the rotating reflector which is rotatably driven by the motor about said axis of rotation. The optical block comprises a light source for producing a bundle of light rays directed upon the rotating reflector as well as a light receiver for processing the light pulses.

With this equipment there is achieved the beneficial result that, on the one hand, there is afforded the possibility of optimumly utilizing the precise and digital time measurement, and, on the other hand, the measured result cannot be influenced by any radial shifting of the axis of the pivotable shaft which may possibly arise and existing within the range of the manufacturing tolerances nor by reaction forces or temperature fluctuations.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1:
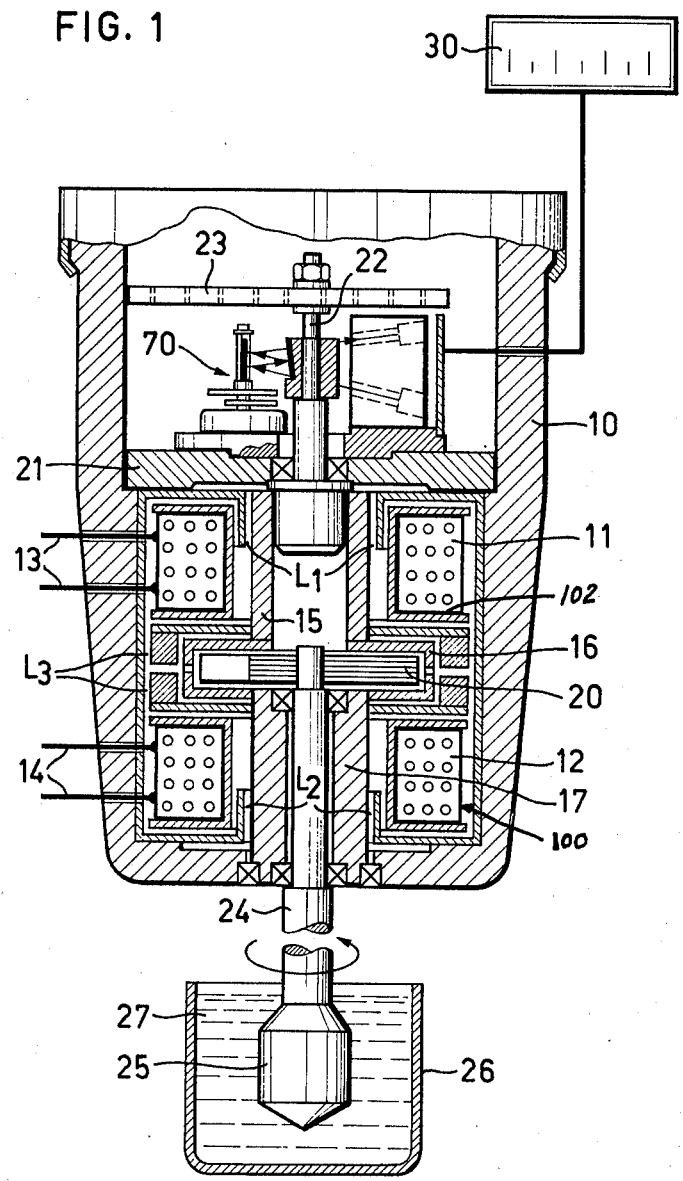
FIG. 1 is an axial sectional view through a rotational viscosimeter equipped with an arrangement of an opto-electrical angle measuring-apparatus according to the invention.

Describing now the drawings, in the arrangement of FIG. 1 it will be seen that within a housing 10 of a viscosimeter there is mounted a synchronous motor, generally indicated by reference character 100, containing the stationary windings 11 and 12 and appropriate current supply lines 13 and 14 respectively. The magnetic flux induced in the stator windings 11 and 12 by the infed alternating current is transmitted by means of suitable air gaps $L_1$, $L_2$ and $L_3$ to the interconnected ferronmagnetic parts 15, 16, 17 of the stator 102 of the synchronous motor 100. This stator 102 is operatively connected at one side by means of the stator part 17, through the intermediary of a rotatable shaft 24, with a rotatable body or element 25 attached to the free end of such rotatable shaft 24, as best seen by referring to FIG. 1. The stator 102 is operatively connected at the other side by means of its stator part 15 with a positively or form-lockingly connected shaft 22 which is rotatably mounted in a plate 21. Attached to the shaft 22 is a torsion spring 23 or equivalent structure. The rotor 20 of the motor 100 is mounted within the stator parts 15, 16 and 17. The shaft 24 is attached to the rotor 20. The rotational body or element 25 which is exchangeably connected in any convenient fashion to the free end of the shaft 24 can be immersed into a vessel or container 26 filled with a medium 27 the viscosity of which is to be measured.

Furthermore, FIG. 1 additionally illustrates an angle measuring-apparatus 70, details of which will be considered more fully hereinafter, which is attached by any suitable means to the plate 21 as will also be explained more fully during the course of this disclosure.

Figure 2:
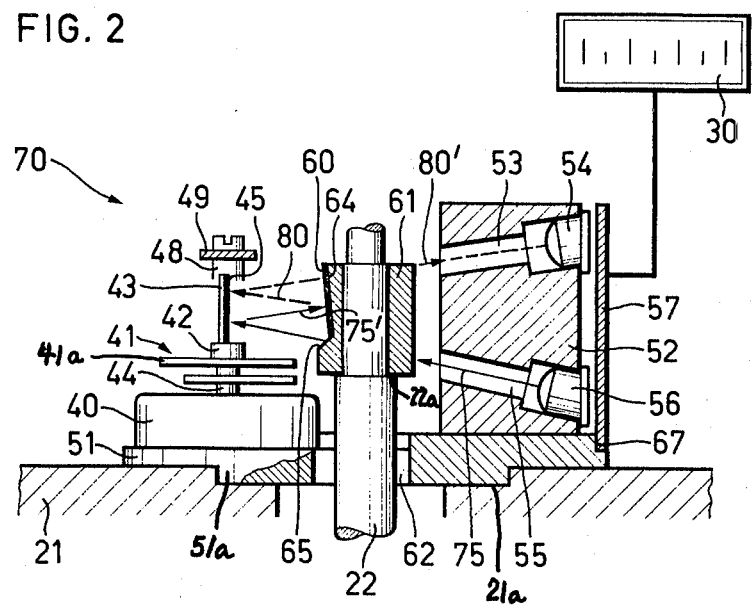
FIG. 2 is an enlarged side view, partially in section, of the angle measuring-apparatus showing the optical system or block in an offset disposition in order to improve the illustration.

Turning attention now to FIG. 2 the angle measuring-apparatus 70 is shown on an enlarged scale, in side and partially sectional view therein. There will be recognized a flange or plate 51 equipped with an opening 62 which is secured in any convenient fashion to the plate 21. To this end, the flange or plate 51 may be provided with a stepped portion or protruding part 51a which is mountingly received in an appropriately configured recess 21a of the plate 21. The shaft 22 of the viscosimeter piercingly extends through the opening 62 of the flange or plate 51. This shaft 22 is provided at its upper region with a stepped portion 22a which serves as a contact or support surface for a hub member 61 or equivalent structure which is fitted onto the end of such shaft 22 and can be rigidly connected for rotation therewith by any suitable means.

Continuing, and as viewed from the upper edge or surface of the hub 61, it will be seen that such is provided with a downwardly directed recess or inset portion 63 equipped with a stepped portion or shoulder 65. The front face or surface 64 of the recess 63, in the illustrated exemplary embodiment, preferably extends from the upper surface of the hub 61 so as to incline slightly inwardly and the shoulder 65 is formed so as to incline slightly outwardly and downwardly towards the outer surface or circumference of such hub 61. This recess or inset portion 63 serves to receive a reflector or mirror 60 which is attached in any convenient fashion to the front surface or face 64 thereof.

Now in spaced relationship from and essentially parallel to the axis of the shaft 22 there is mounted and conveniently attached to the flange 51 a motor 40, preferably a synchronous motor, equipped with a shaft 44. A schematically illustrated mechanical filter 41, for instance constructed of an oscillating mass and a spring, merely generally indicated by reference character 41a, is arranged at the motor shaft 44. Above the filter 41 there is provided a hub 42 or equivalent structure equipped with a web 43, the hub 42 being slipped onto the shaft 44. A reflector or mirror 45 is secured to the web 43. Yet, the web 43 can also be constructed for receiving two or more reflectors, as will be discussed more fully in conjunction with the embodiments of FIGS. 4 and 5.

Now to both sides of the motor 40 there is arranged a respective upright bolt 48 or equivalent structure which is fixedly connected with the flange 51. These bolts serve to support bracket 49 arranged at a slight spacing above the rotating reflector 45 and the web 43. The bracket 49 is attached by screws 47 or the like with the bolts 48, to thereby secure the hub 42 together with the reflector 45 attached thereto against falling out.

Also there has been shown in FIG. 2 a stationary optical block or system 52, illustrated in sectional view and shown offset from its actual position at which it is mounted upon the flange or plate 51 in order to simplify the illustration of the drawing. This optical block of system 52 contains a light source or transmitter 56 with which there is associated a suitably arranged light passage or channel 55 which is directed towards the reflector 45 and a light receiver 54 whose central axis is disposed above that of the light source 56. The light receiver 54 also has associated therewith a light passage or channel 53 which also is directed towards the reflector 45. Both of these light conducting-channels 53 and 55 should possess as long as possible construction, in order to thereby provide for a confined and limited beam or bundle of light rays, although this requirement can be however equally fulfilled by providing an appropriately arranged optical system or lens arrangement.

Figure 3:
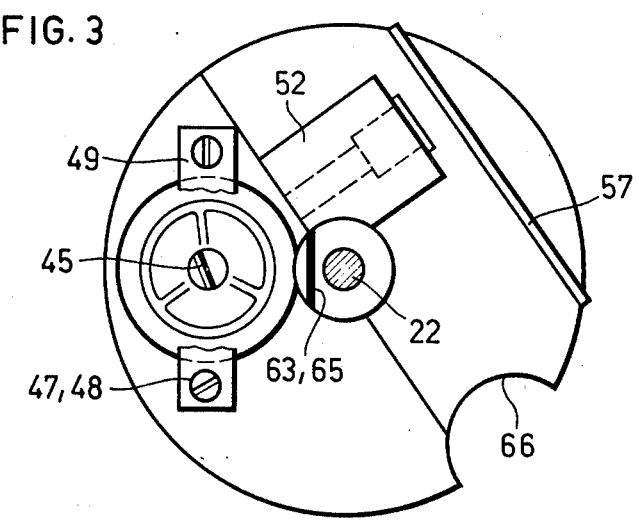
FIG. 3 is a top plan view of the apparatus shown in FIG. 2, wherein the optical system or block has been shown in the correct functional position.

In FIG. 3 there is shown in top plan view and closer to reality the proper functional position and geometric arrangement of the optical block or system 52 having the light source 56 and the light receiver 54 in relation to the rotating reflector 45 as well as the arrangement of the reflector 45 with respect to the reflector 60 which is to be deflected through a predetermined angle. A terminal plate 57 (printed circuit) is attached by any suitable means, for instance adhesively bonded, to a shoulder 67 provided at the flange 51, this shoulder 67 preferably extending substantially parallel to the rear face of the optical block 52. Additionally, a recess or cutout 66 is provided at the flange or plate 51 and serves for the throughpassage of not particularly illustrated current supply lines connected with the motor of the viscosimeter.

Figure 4:
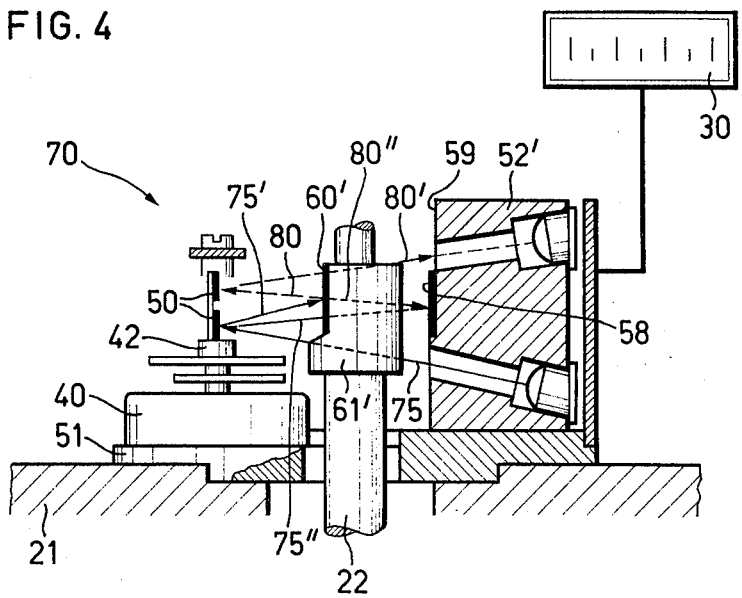
FIG. 4 is a side view, partially in section, of a variant construction of angle measuring-apparatus, again showing the optical system or block in an offset disposition to improve the clarity of illustration.
Figure 5:
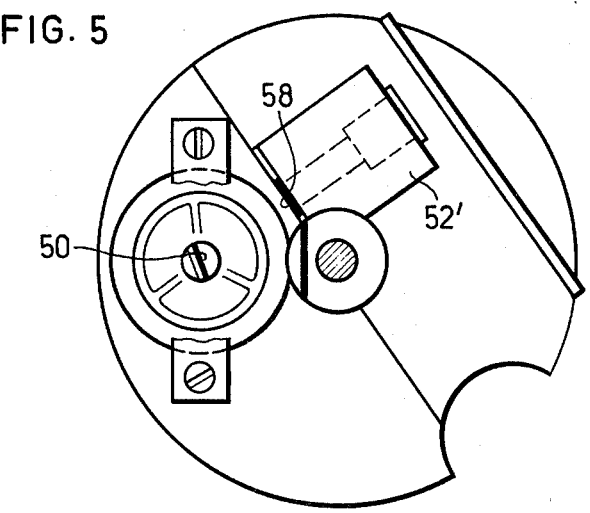
FIG. 5 is a top plan view of the apparatus portrayed in FIG. 4, but this time illustrating the optical system or block in the correct position required for the function of the equipment.

Regarding the variant embodiment of angle measuring-apparatus 70 shown in FIGS. 4 and 5, such differs on the one hand from the apparatus construction of FIGS. 2 and 3 in that there is arranged at the front face 59 of the block 52', preferably between both of the light channels 53 and 55, an additional stationary reflector 58. A further difference resides in that here there is secured at the hub 42 rotatably driven by the motor 40 either two separate reflectors 50 or one reflector 50 which is covered at its center so as to in effect form two separate reflectors. Still a further difference is that the reflector 60' attached to the hub 61' in this case is not positioned at an inclination, rather extends substantially parallel to the central axis of the shaft 22. Since otherwise this embodiment of FIGS. 4 and 5 is generally similarly constructed as the embodiment discussed above with regard to FIGS. 2 and 3 there have been used for the most part the same reference characters to denote the same or analogous components.

At this point mention is made of the fact that the path of the light rays or beams indicated in FIGS. 2 and 4 have been shown purely to show the course of the light rays and the angular position or relation of the individual light beams to one another does not correspond to reality owing to the offset shown position of the optical blocks or systems 52 and 52' of FIGS. 2 and 4 respectively, which it will be recalled have been thusly illustrated for clarity purposes, with the functionally correct positioning of such components as substantially encountered in practice being more truely representatively shown in FIGS. 3 and 5.

Figure 6:
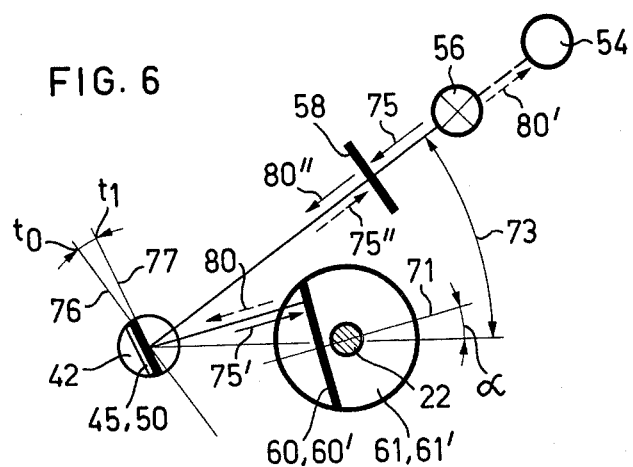
FIGS. 6, 7 and 8 respectively illustrate different light beams or rays which have been projected as a function of time $t$ by a rotating reflector upon a pivotable projection plane and reflected back therefrom.
Figure 7:
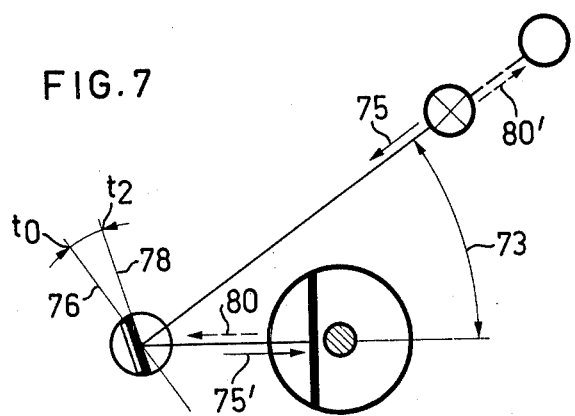
Figure 8:
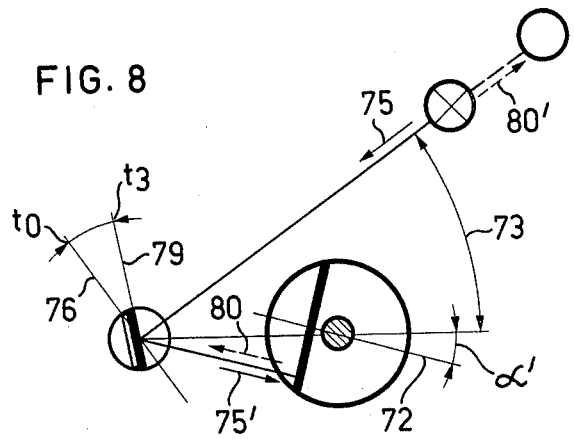

In FIGS. 6 to 8 there have been illustrated the individual light rays or beams 75, 75', 75" and 80, 80' and 80" which are propagated by the light source or transmitter 56 and reflected back to the light receiver 54. Directional arrows have been conveniently employed along side the light rays or beams represented by the aforementioned reference characters.

The course of the individual light rays or beams during the measuring- and evaluation operations performed with the apparatus described in conjunction with a rotational viscosimeter is as follows.

Depending upon the frequency of the excitation current the rotor 20 has imparted thereto an appropriate rotational speed, by means of which the rotatable body or element 25 immersed in the vessel or container 26 filler with the medium whose viscosity is to be checked is thus rotated, and hence, depending upon the viscosity of such medium, this rotatable body 25 is braked to a greater or lesser extent. The braking moments which thereby occur are transmitted to the stator part 15, so that the shaft 22 which is rigidly connected for rotation with such stator part 15 as well as the hub 61 provided with the reflector 60 and attached to the shaft 22 are rocked out of their rest position, against the restoring force of the torsion spring 23, in proportion to the effective viscosity of the medium.

Starting from the rest position, where the shaft 22 together with the reflector 60 assumes for instance the orientation shown in FIG. 6 and the reflector 45 is located in the position indicated by the line 76, corresponding to the point in time $t_o$, and extending at right angles to the stationary light source 56 as well as the light source 54, the light beam 75 which is emitted by the light source 56 and impinges the reflector 45 at right angles is then reflected to the light receiver 54 in the form of the light beam 80', thereby producing an electrical signal. In the time interval from $t_o$ to $t_1$ the reflector 45 driven by the motor 40 rotates such that the light beam 75 is reflected at the point in time $t_1$, indicated by the line 77, in the form of the light beam 75' onto the reflector 60 and from that location is reflected back in the form of the light beam 80 via the reflector 45 as a light beam 80' to the light receiver 54, so that again there is produced an electrical signal. During each revolution of the reflector 45 this cycle repeats, and in the time between $t_1$ and $t_o$ the light beam 75, without producing an electrical signal, is reflected into the free space or surroundings.

Now if there occurs a braking moment at the shaft 22 and the reflector 60 is pivoted or rocked out of the rest position illustrated in FIG. 6, for instance into one of the two positions shown in FIGS. 7 or 8, then from the time of the first electrical signal until there occurs a reflection and thus there is produced a further electrical signal, there either expires the time interval $t_o$ to $t_2$ indicated in FIG. 7 by the line 78, or, however, the time $t_o$ to $t_3$ indicated by the line 79 in FIG. 8.

Now with the apparatus according to the variant construction of FIGS. 4 and 5 the operation is analogous to the operation previously described in conjunction with FIGS. 6 to 8, however the beam of light for the first electrical signal travels in such a manner that the light beam 75 emanating from the light source 56 at the point in time $t_o$ and directed at right angles to the reflector 50 is reflected by the lower part of the reflector 50 or the lower reflector 50, as the case may be, in the form of the light beam 75" to the reflector 58, only illustrated in FIG. 6 for the variant embodiment, and then is reflected by the reflector 58 in the form of the light beam 80" by means of the upper part of the reflector 50 or the upper reflector 50, again as the case may be, in the form of the light beam 80' to the light receiver 54. When there occurs a braking moment the shaft 22 together with the reflector 60' is likewise rocked. Thus there transpires from the time of the first electrical signal until there occurs a reflection and there is thus formed a further electrical signal, again either the time interval $t_o$ to $t_1$ or $t_o$ to $t_2$ or $t_o$ to $t_3$ respectively. The path of the light rays travels, however, in such a manner that starting from the light source 56 the light beam 75 is reflected by the lower part of the rotating reflector 50 or the lower reflector 50, as the case may be, in the form of the light beam 75' to the rocked reflector 60' and from that location is reflected as a light beam 80 by means of the upper part of the reflector 50 or the upper reflector 50, as the case may be, in the form of the light beam 80' to the light receiver 54.

For both of the exemplary embodiments according to FIGS. 2, 3 and FIGS. 4, 5 respectively, the time interval $t$ which prevails between the electrical signals, on the one hand, is dependent upon the geometric arrangement of the optical block 52 or 52' respectively, equipped with the light source 56 and the light receiver 54 in relation to the stationary reflector 45 and 50 respectively (FIGS. 6 to 8), which geometric arrangement has been indicated by the line 73, and, on the other hand, is proportional to the deflection angle $\alpha$ and $\alpha'$ of the reflector 60 and 60', respectively, which is disposed between the region indicated by the lines 71 and 72 and corresponding to the degree of the measured value or magnitude. Tests have shown that the optimum measurement results can be obtained if there is maintained an angular position of 25° to 45°, which angular range is indicated by the line or arc 73.

By virtue of the additional reflector 58 which is appropriately stationarily arranged at the front face or side of the optical block 52' of the variant embodiment of FIGS. 4 and 5, it is possible in contrast to the embodiment according to FIGS. 2 and 3, for the light beam 75, 75" and 80, 80" delivered by the light source 56 for the first electrical signal and reflected by the reflectors 50, 58 to the light receiver 54 as well as the light beam 75, 75' and 80, 80" transmitted from the light source 56 when a braking moment occurs and reflected by the reflectors 50, 60' to the light receiver 54, to be of the same length, thereby rendering possible an even more exact evaluation.

Depending upon the viscosity of the medium which is to be checked it is readily possible for there to occur a reflection and thus for there to be produced an electrical signal with both embodiments, also between both of the positions illustrated in FIGS. 6 to 8 and indicated by the deflection angles $\alpha$ and $\alpha'$ respectively.

The electrical signals are transmitted by means of any suitable and therefore not particularly illustrated conductors or lines from the terminal plate 57 (e.g. printed circuit board) to a suitable evaluation device 30 shown in FIGS. 1, 2 and 4. The evaluation device 30 can be, for instance, a conventional cycle or period-measuring device, a cathode ray-oscillograph or the like.

With the described angle measuring-apparatus the viscosity of a medium can be determined with optimum operational reliability and while maintaining the required measurement accuracy with appreciably smaller deflection angle, whereby both for the viscosity regulation or control as well as also with different measuring speeds, i.e. rotational speeds of the rotatable body, there can be attained a considerably shorter measuring time or duration.

The evaluation can be accomplished with such opto-electrical angle measuring-apparatus both directly at the viscosimeter as well as also at an arbitrary distance therefrom and therefore is especially suitable also for use with viscosimeters which are installed in industrial installations.

While there are shown and described present preferred embodiments of the invention, it is to be distinctly understood that the invention is not limited thereto, but may be otherwise variously embodied and practiced within the scope of the following claims.

Accordingly, what we claim is:

1. An apparatus for the opto-electrical determination of a measured magnitude at a viscosimeter, especially at a rotational viscosimeter, comprising:
   a motor containing a stator and a rotor;
   a rotatable body immersible in a medium, the viscosity of which is to be measured;
   means for connecting the rotatable body with said rotor of said motor;
   a pivotably mounted shaft rigidly connected for rotation with said stator of said motor;
   a torsion spring for exerting a restoring force upon said pivotably mounted shaft;
   means for obtaining a series of light pulses independent of the measured magnitude and a further series of light pulses dependent upon said measured magnitude;
   said means for obtaining said respective series of light pulses comprising:
      a first reflector provided for said pivotably mounted shaft;
      at least one rotatably driven second reflector;
      a drive motor for driving said rotatably driven second reflector about an axis of rotation;
      said rotatably driven second reflector being arranged in spaced relationship from and essentially parallel to the axis of said pivotably mounted shaft;
      a stationary optical block cooperating with said rotatably driven second reflector;
      said optical block comprising a light source for producing a light beam directed to impinge upon said rotatably driven second reflector and a light receiver for processing the light pulses.

2. The apparatus as defined in claim 1, wherein:
   said optical block is positioned, viewed with respect to the axis of rotation of said rotatably driven second reflector, such that it is located in a predetermined angular position with respect to a plane containing the lengthwise axis of said pivotably mounted shaft;
   said optical block further comprising a first light channel for receiving the light source and a second light channel for receiving the light receiver;
   both of said light channels being directed towards said rotatably driven second reflector.

3. The apparatus as defined in claim 2, wherein:
   said predetermined angular position is in a range between 25° and 45°.

4. The apparatus as defined in claim 1, further including:
   means for mounting said first reflector at said shaft in accordance with the light beam which is to be reflected and non-rotatable with respect to said shaft such that a reflecting surface of said first reflector which confronts the rotatably driven reflector is slightly inclined with respect to said shaft.

5. The apparatus as defined in claim 1, wherein:
   said optical block includes a front surface;
   an additional reflector carried by said front surface of said optical block; and
   said rotatably driven reflector comprises a two-part reflector structure.

6. The apparatus as defined in claim 5, wherein:
   said first reflector includes a reflecting surface extending substantially parallel to the axis of rotation of said rotatably driven reflector.

7. The apparatus as defined in claim 1, further including:
   mechanical filter means provided for said drive motor.

8. The apparatus as defined in claim 7, wherein:
   said mechanical filter means comprises an oscillating mass and a spring.

9. The apparatus as defined in claim 1, further including:
   mechanical filter means provided for said drive motor;
   common flange means at which there are arranged said optical block, said drive motor, said mechanical filter means and said rotatably driven reflector.

10. An apparatus for the opto-electrical determination of a measured magnitude at a viscosimeter, especially at a rotational viscosimeter, comprising:
   a motor containing a stator and a rotor;
   a rotatably body immersible in a medium, the viscosity of which is to be measured;
   means for connecting the rotatable body with said rotor of said motor;
   a pivotably mounted shaft connected for rotation with said stator of said motor;
   means for exerting a restoring force upon said pivotably mounted shaft;
   means for obtaining a series of light pulses independent of the measured magnitude and a further series of light pulses dependent upon said measured magnitude;
   said means for obtaining said respective series of light pulses comprising:
      a first reflector provided for said pivotably mounted shaft;
      at least one rotatably driven second reflector;
      drive means for driving said rotatably driven second reflector about an axis of rotation;
      said rotatably driven second reflector being arranged in spaced relationship from and essentially parallel to the axis of said pivotably mounted shaft;
      stationary optical means positioned to cooperate with said rotatably driven reflector;
      said optical means comprising a light source for producing a light beam directed to impinge upon said rotatably driven second reflector and a light receiver for processing the light pulses.

* * * * *